(12) United States Patent
Martinez-Martin et al.

(10) Patent No.: US 10,564,182 B2
(45) Date of Patent: Feb. 18, 2020

(54) MEASURING DEVICE AND METHOD FOR DETERMINING MASS AND/OR MECHANICAL PROPERTIES OF A BIOLOGICAL SYSTEM

(71) Applicants: UNIVERSITÄT BASEL, Basel (CH); ETH Zurich, Zürich (CH)

(72) Inventors: David Martinez-Martin, Basel (CH); Daniel J. Mueller, Basel (CH); Sascha Martin, Basel (CH); Christoph Gerber, Richterswil (CH); Benjamin Bircher, Bern (CH)

(73) Assignees: Universität Basel, Basel (CH); ETH Zürich, Zürich (CH)

( * ) Notice: Subject to any disclaimer, the term of this patent is extended or adjusted under 35 U.S.C. 154(b) by 526 days.

(21) Appl. No.: 15/119,432

(22) PCT Filed: Feb. 17, 2015

(86) PCT No.: PCT/EP2015/000350
§ 371 (c)(1),
(2) Date: Aug. 17, 2016

(87) PCT Pub. No.: WO2015/120992
PCT Pub. Date: Aug. 20, 2015

(65) Prior Publication Data
US 2017/0052211 A1    Feb. 23, 2017

(30) Foreign Application Priority Data

Feb. 17, 2014 (EP) .................................... 14000560
Dec. 16, 2014 (EP) .................................... 14004244

(51) Int. Cl.
*G01N 29/02* (2006.01)
*G01Q 30/02* (2010.01)
(Continued)

(52) U.S. Cl.
CPC ......... *G01Q 30/025* (2013.01); *B81B 3/0029* (2013.01); *G01G 9/00* (2013.01);
(Continued)

(58) Field of Classification Search
CPC ...... G01Q 30/025; G01Q 9/00; G01Q 10/045; B81B 3/0029; G01N 21/6458;
(Continued)

(56) References Cited

U.S. PATENT DOCUMENTS 6,330,824 B1    12/2001  Erie et al.
2006/0075803 A1*  4/2006  Boisen ................ G01N 29/036
                                                    73/31.06
(Continued)

FOREIGN PATENT DOCUMENTS

JP    2007-85953 A     4/2007
JP    2013-540127 A    10/2013
(Continued)

OTHER PUBLICATIONS

Kidong Park et al. "Living cantilever arrays' for characterization of mass of single live cells in fluids" The Royal Society of Chemistry, Lab Chip, Jun. 11, 2008, vol. 8, 1034-1041.
(Continued)

*Primary Examiner* — Nicole M Ippolito
(74) *Attorney, Agent, or Firm* — Walter | Haverfield LLP; Sean F. Mellino; D. Peter Hochberg

(57) ABSTRACT

The invention relates to a measuring device and a method for determining mass and/or mechanical properties of a biological system.

20 Claims, 9 Drawing Sheets

(51) Int. Cl.

| | |
|---|---|
| *G01N 21/64* | (2006.01) |
| *G02B 21/00* | (2006.01) |
| *G02B 21/16* | (2006.01) |
| *G01N 21/65* | (2006.01) |
| *G02B 21/26* | (2006.01) |
| *B81B 3/00* | (2006.01) |
| *G01G 9/00* | (2006.01) |
| *G02B 21/32* | (2006.01) |

(52) U.S. Cl.
CPC ......... *G01N 21/6458* (2013.01); *G01N 21/65* (2013.01); *G02B 21/0088* (2013.01); *G02B 21/16* (2013.01); *G02B 21/26* (2013.01); *G02B 21/32* (2013.01); *B81B 2201/0214* (2013.01); *B81B 2201/047* (2013.01); *B81B 2203/0118* (2013.01); *G01N 2201/06113* (2013.01)

(58) Field of Classification Search
CPC .... G02B 21/0088; G02B 21/16; G02B 21/26; G02B 21/32
USPC ............................ 850/9, 52, 56, 59, 60, 61
See application file for complete search history.

(56) References Cited

U.S. PATENT DOCUMENTS

| | | | |
|---|---|---|---|
| 2006/0219010 A1 | 10/2006 | Ilic et al. | |
| 2008/0245135 A1 | 10/2008 | Aubin et al. | |
| 2009/0101815 A1 | 4/2009 | Ohtsuka | |
| 2010/0013456 A1* | 1/2010 | Montelius | G01G 3/16 324/76.51 |
| 2010/0139406 A1 | 6/2010 | Stievater et al. | |
| 2011/0070604 A1* | 3/2011 | Gimzewski | B82Y 35/00 435/29 |

FOREIGN PATENT DOCUMENTS

| | | |
|---|---|---|
| WO | 9605531 A1 | 2/1996 |
| WO | 2012059828 A2 | 5/2012 |
| WO | 2013003864 A1 | 1/2013 |
| WO | 2015120991 A1 | 8/2015 |

OTHER PUBLICATIONS

Kidong Park et al. "Measurement of adherent cell mass and growth" PNAS, Nov. 30, 2010, vol. 107, No. 48, pp. 20691-20696.

Sungmin Son et al. "Direct observation of mammalian cell growth and size regulation" Nature America, Inc., Sep. 2012, vol. 9, No. 9, pp. 910-913.

M.F. Khan et al. "Fabrication of resonant micro cantilevers with integrated transparent fluidic channel" Microelectronic Engineering, Feb. 22, 2011, vol. 88, pp. 2300-2303.

Communication from the European Patent Office dated Sep. 6, 2017 for corresponding European Patent Application No. 15 717 089.5.

Drew R. Evans et al., "Laser Actuation of Cantilevers for Picometre Amplitude Dynamic Force Microscopy", Scientific Reports, published Jul. 4, 2014, vol. 4:5567, pp. 1-7.

International Search Report for corresponding PCT/EP2015/000349 dated Jun. 29, 2015.

Written Opinion of the International Searching Authority for corresponding PCT/EP2015/000349 dated Jun. 29, 2015.

Alex Berquand "Combined Optical and SPM Microscopy" Retrieved from Internet: https://www.bruker.com/fileadmin/user_upload/8-PDF-Docs/SurfaceAnalysis/AFM/Webinars/Combined-Optical-AFM_webinar_slides_120118.pdf, Jan. 2012.

R. Kassies et al. "Combined AFM and confocal fluorescence microscope for applications in bio-nanotechnology" Journal of Microscopy, Jan. 2005 pp. 109-116, vol. 217(1).

Andreea Trache et al. "Atomic force-multi-optical imaging integrated microscope for monitoring molecular dynamics in live cells" Journal of Biomedical Optics, Nov./Dec. 2005 p. 064023, vol. 10(6).

International Search Report for corresponding PCT/EP2015/000350 dated Jun. 30, 2015.

Written Opinion of the International Searching Authority for corresponding PCT/EP2015/000350 dated Jun. 30, 2015.

J.W. Park et al. "Continuous monitoring of insulin attachment kinetics on photothermally actuated microcantilever biosensor" Transducers 2009: International Solid-State Sensors, Actuators and Microsystems Conference, Jun. 21-25, 2009 pp. 979-982.

Nathan P. Malcolm et al. "Simulation of a piasmonic tip-terminated scanning nanowire waveguide for molecular imaging" Applied Physics Letters, American institute of Physics, Nov. 10, 2008 p. 193101, vol. 93.

J.P. Cleveland et al. "A nondestructive method for determining the spring constant of cantilevers for scanning force microscopy" Review of Scientific Instruments, American Institute of Physics, Oct. 19, 1992 pp. 403-405, vol. 64(2).

Shuhei Nishida, Photothermal Excitation of a Single-crystal Silicon Cantilever, Kenkyu Sokuho 62, No. 3 (2010): 53-56.

Office Action from the Japanese Patent Office dated Dec. 11, 2018 for corresponding Japanese Patent Application No. 2016-569003.

Shuhei Nishida, Photothermal Excitation of a Single-crystal Silicon Cantilever, Kenkyu Sokuho 62, No. 3 (2010), pp. 53-56.

* cited by examiner

MEASURING DEVICE AND METHOD FOR DETERMINING MASS AND/OR MECHANICAL PROPERTIES OF A BIOLOGICAL SYSTEM

CROSS-REFERENCE TO RELATED APPLICATIONS

This application is a 371 National Stage application of International Application No. PCT/EP2015/000350 filed on Feb. 17, 2015, which claims priority of European Patent (EP) application Serial Number 14000560.4 filed on Feb. 17, 2014 and European Patent (EP) application Serial Number 14004244.1 filed on Dec. 16, 2014, all of which are incorporated herein by reference in their entireties.

BACKGROUND OF THE INVENTION

Field of the Invention

The invention relates to a measuring device and a method for determining mass and/or mechanical properties of a biological system.

Description of the Prior Art

Measuring devices for determining mass and/or mechanical properties of biological systems are known from the state of the art.

In Park K, Jang J, Irimia D, Sturgis J, Lee J, Robinson J P, Toner M, Bashir R. *Living cantilever arrays for characterization of mass of single live cells in fluids*. Lab on a Chip. 8:1034-41 (2008) cantilever arrays are developed to determine mass of cells in solution. These arrays are formed by two sets of cantilevers opposing each other. External sinusoidal power sources are connected to the opposing cantilever sets with a phase shift of 180° in order to generate a nonuniform electric field, which captures cells by dielectrophoresis. There is no active excitation method to oscillate the cantilevers. The cantilevers vibrate only due to thermal noise, which decreases the sensitivity and temporal resolution of this device to measure mass changes. Before starting mass measurements, several days, usually three days, are required for the cells to grow on the cantilevers. That means random cells are selected for the experiments. Due to the design of this device, its use is not compatible with modern optical microscopy techniques for biology, for example differential interference contrast (DIC), fluorescence, confocal or phase contrast microscopy. These techniques are very important in biology since they give additional morphological and functional information about the characterized cell or biological system.

The work of Park K, Millet L J, Kim N, Li H, Jin X, Popescu G, Alum N R, Hsia K J, Bashir R. Measurement of adherent cell mass and growth. PNAS, 107: 20691-6 (2010) shows a device that uses micro-membrane resonators to determine the mass and mechanical properties of single adherent cells in fluid. The membranes are actively excited using the Lorentz's force. To do that the membranes are immersed into a uniform magnetic field and an alternating electrical current flows through the membranes. The movement of the membrane is detected by using a laser Doppler interferometer (LDI). In order to attach cells to the membranes, cells are cultured on the device. Doing so, some cells will randomly adhere to the top of the membranes. Once the cells are injected into the device, at least two hours of waiting time are required before starting the measurements, which importantly limits the cellular processes to be studied. This system is compatible with fluorescence but not with DIC or phase contrast microscopy.

The device in S. Son, A. Tzur, Y. Weng, P. Jorgensen, J. Kim, M. W. Kirschner, S. R. Manalis. *Direct observation of mammalian cell growth and size regulation*. Nat. Methods. 9:910-2 (2012) is based on a micro-channel resonator, which is a hollow cantilever surrounded by vacuum. Suspended cells floating in a fluid can be pumped into and through the cantilever. When a cell passes by the free end of the cantilever, its buoyant mass increases the total mass of the cantilever, which decreases the resonance frequency of the cantilever. Furthermore, high-resolution fluorescence microscopy can be conducted only for cells passing through a separate reservoir but not when cells pass the mass sensor. This tool is not suitable for adherent cells, since the cells have to be suspended to be able to float through the cantilever. Furthermore, some cellular processes cannot be studied because the device can only detect buoyant masses. Another negative issue of this assay is that both the fluorescence signal (e.g., microscopy) and the buoyant mass of a single cell can be neither acquired continuously over a long period ($>>1$ second) nor simultaneously, making it very difficult to correlate buoyant mass and cell state.

It is an object of the invention to improve these known devices.

SUMMARY OF THE PRESENT INVENTION

According to a first aspect of the invention, a solution to this technical problem is achieved by providing a measuring device for determining mass and/or mechanical properties of a biological system comprising a micro cantilever and an intensity modulated light source preferably a laser exciting the cantilever, wherein the cantilever is functionalized to adhere to the biological system. The measuring device allows determining mass and/or mechanical properties of biological systems such as single cells or small tissues over time and in a physiologically relevant environment. Furthermore, the measuring device is useful to study cell-cell- or cell-tissue-interactions.

A "biological system" is e.g., a cell, a group of cells or a small tissue. The cells can be adherent or non-adherent and of various origins, such as human, animal, yeast and bacteria.

A "light source" is any device which is able to generate electromagnetic signals with wavelengths preferably, but not limited to, the range of 350 nm to 750 nm. The electromagnetic signal can be coherent or non-coherent, monochromatic or non-monochromatic.

To adhere to a biological system such as a cell, the cantilever is functionalized. Functionalization of the cantilever can mean that it is physically or chemically modified in order to exhibit different physical, chemical or biological properties. The functionalization can have different applications as for instance to attach the biological sample to the cantilever or to induce a special behaviour of the sample. As an alternative to a chemical functionalization of the cantilever, also other methods to adhere the biological system to the cantilever are possible. In particular, a micro-channelled cantilever can be used that adheres the biological system to the cantilever by means of a suction mechanism. On rare occasions, specific functionalization will not be necessary, if the biological system adheres to the cantilever without specific binding means because of already existing physical or chemical interaction between sample and cantilever. These alternatives will be considered equivalent to the chemical functionalization by a person skilled in the art.

Single cells (or groups of cells) can be attached to the cantilever by putting them in direct contact with the cantilever. The measuring system can choose and pick up a certain cell among a cell population in culture, thereby allowing a targeted measurement of mass and/or mechanical properties of a chosen cell. Also a measurement of non-adherent cells is possible, since they can be immobilized at the end of the cantilever. This allows a measurement in a very short time period, because measurement can be commenced as soon as the cell is picked up. A measurement can therefore usually start within seconds or in a maximum of a few minutes. The measuring device is capable of directly measuring total mass, since the biological system attached to the cantilever adds all its mass to the mass of the cantilever modifying its resonance frequency. In addition, the dry mass of the biological sample can be detected by optical methods compatible with our device such as SLIM (Spatial Light Interference Microscopy). The possibility of directly detecting the total mass of a cell is crucial to understand cell cycle regulation or any other process in which the cell could uptake or release water. It is important to note that other state of the art systems are not able to detect the total mass of a single cell but its buoyant mass only. By measuring the buoyant mass of a single cell in two fluids with different densities and assuming that the volume and mass of the cell is kept constant under these conditions (which could be not the case), those systems can try to estimate the total mass. However, the requirement of changing the medium in which the cell is living for every measurement can be very stressful for the cells and definitely it is far away from physiological conditions.

It can also be used to study mechanical properties of cells such as adhesion, stiffness or rheological properties. Adhesion of a cell with respect to a certain substrate or to another cell can be measured by first immobilizing a cell on the cantilever and then making this cell contact the substrate or cell for a specific amount of time. After the previous time, the system withdraws the cell on the cantilever from the substrate or cell and measures the force required for that process by measuring the deflection of the cantilever. The stiffness of a cell can be measured by confining a cell between the cantilever and a substrate, and then analysing the deflection of the cantilever while the distance between the base of the cantilever and the substrate is modified in a controlled way. The stiffness of the cell can be also determined by attaching a cell on the cantilever and setting up the cantilever far away from the substrate (usually tens of microns or more). In these conditions the cantilever is oscillated at the resonance frequency and changes of its quality factor can be correlated with changes of the cell's stiffness. However other possibilities to extract mechanical properties can be also applied. Furthermore, the measuring device is able to bring a single cell in contact with or close to another cell or tissue, in order to study the cellular interactions between cells and tissues.

The measuring device uses the principle of photothermal excitation of the cantilever, thereby allowing the measuring device to increase the mass sensitivity and the temporal resolution. To directly excite the cantilever and not any other part of the device, which could introduce noise, an intensity modulated light source preferably a laser is addressed on the cantilever. This laser produces a very localized, modulated heating that accordingly excites the cantilever. The laser can be digitally and/or analogically modulated. The cantilever is absorbent i.e. also partially absorbent for the wavelength of the light source. The material of the cantilever can be silicon, but other materials with similar properties may be used as well. The cantilever does not require any coating layer to be excited with the laser, however this may also be fully or partially coated with metals. Preferably the region where the biological sample is going to be placed is not coated with metal.

To increase the mass sensitivity, the functionalized side of the cantilever may be positioned close to the free end of the micro-cantilever. Accordingly, the cantilever may be fully or partially functionalized.

The detection of the mass and/or mechanical properties of the biological system comes from the analysis of a driven movement of the cantilever. The resonance frequency of the cantilever is a function of the mass of the cantilever. When a biological sample is attached to the cantilever, the mass of the cantilever changes, which leads to changes in its resonance frequency. Checking the resonance frequency of the system based on the cantilever and the attached biological sample, the mass changes of the biological sample are tracked. From a comparison between the resonance frequency of the cantilever without the attached sample and the cantilever with the attached sample, the mass of the attached sample can be obtained. Furthermore, the measuring device is able to evaluate how fast the energy transferred to the cantilever is dissipated, which is a measurement of the dimensionless magnitude called quality factor or Q-factor. Both magnitudes, resonance frequency and Q-factor, can be influenced by the mechanical properties of the sample attached to the cantilever, which allows the device to be sensitive to those changes as well. Furthermore, the use of additional parameters to extract information is possible e.g., the phase (delay between excitation signal and the cantilever response) and the amplitude of the movement of the cantilever.

The system used to read out the movement of the cantilever is not as crucial as the cantilever excitation method and can be done using a variety of systems for example: beam deflection, piezo-resistive detection, Doppler interferometry, etc. This system allows acquiring for each frequency two main magnitudes of the movement of the cantilever: the amplitude and the phase. The amplitude is the maximum elongation of the cantilever for a given frequency; the phase is related to the response delay of the cantilever with respect to the excitation signal. Respective computation of the acquired information leads to the desired determination of mass and/or mechanical properties.

Advantageously, the cantilever is fully immersed in a buffer solution. This allows detecting the total mass of the biological system under physiological conditions. A fluid cell can be used.

A second and independently inventive aspect of the invention relates to a measuring device for determining mass and/or mechanical properties of a biological system comprising a micro cantilever and an intensity modulated light source preferably a laser exciting the cantilever, wherein the cantilever is transparent for a wavelength of the visual spectrum. The cantilever can be partially or totally transparent for the wavelength of the visual spectrum. Advantageously, the region, where the biological sample is going to be placed, is at least partially transparent for a certain wavelength of the visual spectrum. This allows for a combination of the determination of the mass and/or mechanical properties with important optical techniques in cell biology.

Preferably, the part of the cantilever that is close to its free end and partially transparent for at least some wavelength of the visual spectrum is not smaller than 10 µm×10 µm. This window of transparency or partial transparency for at least some wavelength of the visual spectrum is a requirement for the device to be compatible with techniques such as DIC (Differential Interference Contrast) or equivalents techniques, which allow to obtain crucial information about the morphology of the biological sample. These types of techniques, require a special type of illumination, which has to go through the sample and be collected using a special optical microscope located opposite to the illumination source as can be seen in FIG. 2. In addition to the DIC information, the objective shown in FIG. 2 allows our device to get fluorescence information from the sample. However the transparency or partial transparency of the cantilever is not a requirement for the fluorescence information, since the illumination to excite the fluorescence of the sample can be driven through the objective, which collects simultaneously the fluorescence light emitted from the sample.

A third and independently inventive aspect of the invention relates to a measuring device, wherein the measuring device for determining mass and/or mechanical properties of a biological system, comprising a micro cantilever and an intensity modulated light source preferably a laser exciting the cantilever, comprises an optical microscope, in particular a fluorescence microscope, a confocal microscope, a fluorescence energy transfer (FRET) microscope, a DIC and/or phase contrast microscope, all of those in particular as an inverted microscope. This combination of optical techniques in cell biology together with the measurement of the mass and/or the mechanical properties allows for a better understanding of the mass measurements, since the morphology of the cells can be observed. This allows the measuring device to detect cellular mass and correlate this information with cell state and shape.

Although there are Atomic Force Microscopes (AFM) that oscillate the cantilever by photothermal excitation, those systems are not compatible with modern optical techniques such as DIC, fluorescence microscopy, etc. A typical reason is that, in general, those AFM systems use an optical microscope to focus an intensity modulated laser on the cantilever in order to excite (oscillate) the cantilever, which eliminates the possibility of using that microscope for fluorescence imaging. On the contrary, the device described herein is designed in such a way that the intensity modulated laser can be positioned and focused on the cantilever with a special set of optical elements and nanopositioners (see FIG. 3). The optical pathway, allows optical access from the top and bottom of the device without compromising the cantilever excitation mechanism. Additionally the reverse is also true, meaning that the cantilever excitation do not compromise the acquisition of information by modern optical techniques, being both types of systems able to work simultaneously. This fact together with the transparency of the cantilever, cantilever holder and sample holder make the device fully compatible with modern optical techniques. It is important to note that the described device shares some features with systems used for near field optics, however there are major differences. For instance, some systems used for near field optics, have a cantilever and attached to it a waveguide. A laser is focused on the waveguide which has to be very close to a sample (typically several nanometers or tens of nanometers) containing metals in order to excite plasmons. The device described herein does not have a waveguide attached to the cantilever. In addition, the device described herein does not use a laser to induce effects of near field optics such as the excitation of plasmons but to deflect the cantilever over time. Furthermore, the device described herein is able to extract the information from the sample without the need of containing metals. The sample in this device is attached to the cantilever. While determining the total mass of the sample, the cantilever (with the sample attached to it) is located far away from the surface of the petri dish or recipient where the biological sample is cultured in order to avoid possible interactions that could affect the measurements. When working with mammalian cells which can have a diameter when rounded of about 10-20 microns, the distance between the cantilever containing the cell and the surface of the petri dish is typically several tens or hundreds of microns. Moreover, the device described herein utilizes a second laser which is located near the free end of the cantilever in order to read out the deflection of the cantilever. However, this second laser is not compulsory and other systems can be applied such as piezoelectric cantilevers, piezoresistive cantilevers, Doppler interferometers, etc.

The measuring device allows quantifying, at high temporal resolution and in a non-invasive manner, the mass and/or mechanical properties of single cells transitioning through the cell cycle by allowing continuously correlating cellular mass with cell phase and shape. Furthermore, the mass sensor can be customized either to study single cells or a small population of cells.

Preferably the cantilever has a length in the range of 10 μm to 1000 μm. For example for the case of measuring cells with a diameter of approximately 20 μm, the length of the cantilever may be around 75 μm. Furthermore, the cantilever preferably has a resonance frequency in a range of 1 Hz to 10 MHz, preferably in the range of 20 kHz to 1200 kHz, preferably in the range of 20 kHz to 400 kHz when immersed in water. Within this range of the resonance frequency the system can be adapted to measure a single cell of about 1-30 microns in diameter, however smaller or bigger biological systems can be also measured. Finally the cantilever preferably has an oscillation amplitude in the range of 0.01 nm to 300 nm, preferably smaller than 30 nm. To optimize the measuring device it is possible to choose or adapt a cantilever according to the target biological system that will be measured by adapting the cantilever dimensions for different applications.

Preferably light source can be a laser with a wavelength in a range from 350 nm to 750 nm. It may be between 350 nm and 550 nm, preferably between 350 nm and 450 nm. Specifically a wavelength of 405 nm may be used which has the additional advantage that it is far enough from many of the wavelengths used in fluorescence microscopy. However, depending on the cantilever material other wavelengths may be used as well. In particular, the wavelength of the exciting laser is chosen such that it is strongly absorbed by the cantilever. Advantageously the position, diameter and focus of the laser spot on the cantilever may be adjusted and may be located at the base of the cantilever. This maximises the excitation efficiency. The laser spot may be smaller than 100 μm, preferably smaller than 30 μm, preferably smaller than 10 μm in diameter. This size allows exciting the cantilever with high efficiency and at the same time allows having the laser far from the biological system to avoid interactions with the sample. To increase the mass sensitivity, the biological sample is usually positioned close to the free end of the cantilever.

Additionally and advantageously, the spot of the light source preferably the laser on the micro-cantilever and the functionalized side on which the biological system adheres may be located on opposite faces of the cantilever, to prevent any influence on the cells to be studied.

A fourth aspect of the invention relates to a method for determining mass and/or mechanical properties of biological systems comprising the steps of:

a. determining the spring constant of the cantilever
b. exciting the cantilever with a light source preferably a laser at a certain frequency,
c. measuring resonance frequency and/or amplitude and phase of the movement of the cantilever before attaching the biological system
d. approaching the cantilever to a chosen biological system within the sample holder
e. attaching the biological system to the cantilever,
f. measuring resonance frequency and/or amplitude and phase of the movement of the cantilever to compare with the resonance frequency and/or amplitude and phase obtained in step c) and
g. computing mass and/or mechanical properties of the biological system.

If necessary a functionalization of the cantilever is possible before or after step a). Alternatively step a) can be performed after step f). In this case, the cantilever has to be cleaned to remove any rest from the sample before executing step a). In case of the biological system being bound to a surface in step e), the cantilever may be approached to the sample to pick the sample up, and then withdrawn from the surface keeping the sample attached to the cantilever to avoid possible effects of the surface on the resonance frequency of the cantilever. Far away from the surface where the sample was sitting, step f) can be performed. Step f) can be done even after the experiment, since it implies just calculations. Usually 100-200 µm is far enough. Step c) is also done far enough from the surface to avoid possible effects of the surface on the measurement.

Additionally, a measurement may be performed without withdrawal of the cantilever. However, in this case the cantilever is not able to oscillate freely and the obtained information must be interpreted accordingly.

A sweeping process through a frequency spectrum allows to determine the resonance frequency by mapping the movement of the cantilever, i.e. observing amplitude and phase.

This measuring method allows a targeted selection of cells and a specific measurement of the mass and/or mechanical properties. In particular a measurement not only of the buoyant mass but of the total mass of single cells is possible. Therefore, the micro cantilever can be fully immersed in a buffer solution.

The determination of the spring constant of the cantilever in step a) can be performed as follows
a' exciting the cantilever with a laser at a certain frequency,
b' determining the resonance frequency of the cantilever.

This allows for a calibration of the cantilever spring constant, thereby allowing measuring of the total mass. The process using the active excitation by the laser to determine the resonance frequency is very accurate. This process is usually done in air ambient conditions and its aim is to find the spring constant of the cantilever. A very accurate way is by using Sader's method. For that the cantilever is excited using the intensity modulated laser, to scan an interval of frequencies adequate to find the resonance frequency of the cantilever. From the frequency scan the resonance frequency and the quality factor of the cantilever are determined. Using that information together with the density of the air and the dimensions and material of the cantilever, its spring constant can be extracted. However other methods can be also utilized based for instance on measurement of the thermal noise of the cantilever either in air ambient conditions or in liquids, or by analyzing the bending of the cantilever when being pressed with another cantilever whose spring constant is known. When determining the resonance frequency of the cantilever, the cantilever should be far away from the bottom of the sample holder to avoid effects from the surface of the sample holder (usually 100-200 µm is far enough).

However, it is also possible to use a calibration procedure to determine the resonance frequency of the cantilever based on thermal energy vibrations although the accuracy might be much lower. Due to the thermal energy, which is related with the temperature of the cantilever, the cantilever is vibrating at the resonance frequency with very small amplitude. In some cases this amplitude is so small that it can be very difficult to detect. Using for example a spectrum analyser, this movement of the cantilever can be analysed and its resonance frequency measured. This method does not require actively exciting the cantilever, which is difficult when the cantilever is immersed in a liquid. This problem can be overcome as suggested by using an intensity modulated laser, which produces a very clean excitation and response of the cantilever.

The measuring method can further comprise the additional steps performed before step a) of:
a" choosing a biological system,
b" adapting the cantilever dimensions to the chosen biological system.

Tailoring the cantilever to the biological system increases the resolution of the measurement, i.e. adapting the size of the cantilever to the cell type and e.g. its size and/or mass.

One way to adapt the cantilever to the biological system is by cutting down a piece of silicon, for example a big cantilever made of silicon, by using a focused ion beam. This technique allows ablation of materials with very high resolution, but other methods and techniques known to the person skilled in the art could be equally applied to produce the cantilever.

Furthermore, a feedback loop can be used in step f) for tracking mass changes of the biological sample over time with high temporal resolution The use of one or several feedback loops increases the sensitivity and time resolution. In particular, a phase locked loop (PLL) can be used. Therein the phase of the cantilever is used as a control variable and the frequency of the signal to modulate the laser intensity is used as a manipulated variable. The control condition is to find the frequency of the excitation signal that produces a cantilever phase of $\pi/2$. With this system the resonance frequency of the cantilever can be tracked automatically and hence the mass changes can be directly measured.

Furthermore, a second feedback can be used independently or cumulatively to obtain further information about the biological system to be studied. This feedback uses the oscillation amplitude of the cantilever as the control variable and the amplitude of the signal used to modulate the intensity of the laser as the manipulated variable. Thereby it is ensured that the amplitude of the cantilever is kept constant over a long period of time. Doing so, information related to the damping of the system can be acquired.

Fundamental or higher flexural modes of the cantilever can be used.

BRIEF DESCRIPTION OF THE DRAWINGS

The invention will be described in more detail hereinafter with reference to an exemplary embodiment. In the drawing.

DETAILED DESCRIPTION OF THE PRESENT INVENTION

Figure 1:
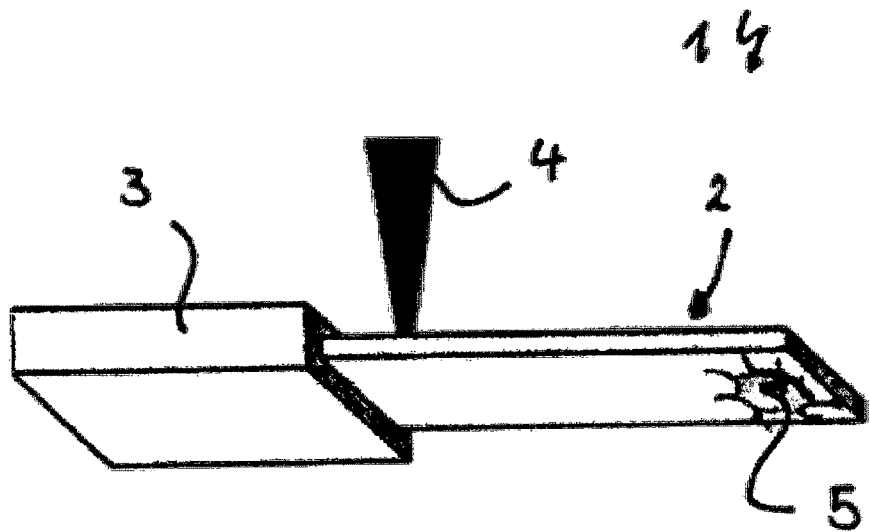
FIG. 1 shows a schematic representation of a measuring device.

The measuring device 1 in FIG. 1 has a cantilever 2 in a fixation 3. The cantilever 2 is excited by the intensity modulated excitation laser 4. This allows for a direct excitation of the cantilever 2 by the intensity modulated laser 4 focused on the cantilever 2. The laser 4 produces very localised modulated heating that excites the cantilever 2. The position, diameter and the focus of this laser spot can be adjusted and it is usually located at the base of the cantilever 2 to maximise the excitation efficiency. A biological system 5 is usually positioned close to the free end of the microcantilever 2 to increase the mass sensitivity. Additionally, to prevent any influence on the biological system to be studied, the excitation laser 4 and the biological system 5, e.g. a cell or several cells, are preferably and advantageously located on opposite faces of the cantilever 2. Therefore, the functionalized side of the cantilever 2 is placed close to this free end. This whole arrangement can be placed within a fluid cell.

Figure 2:
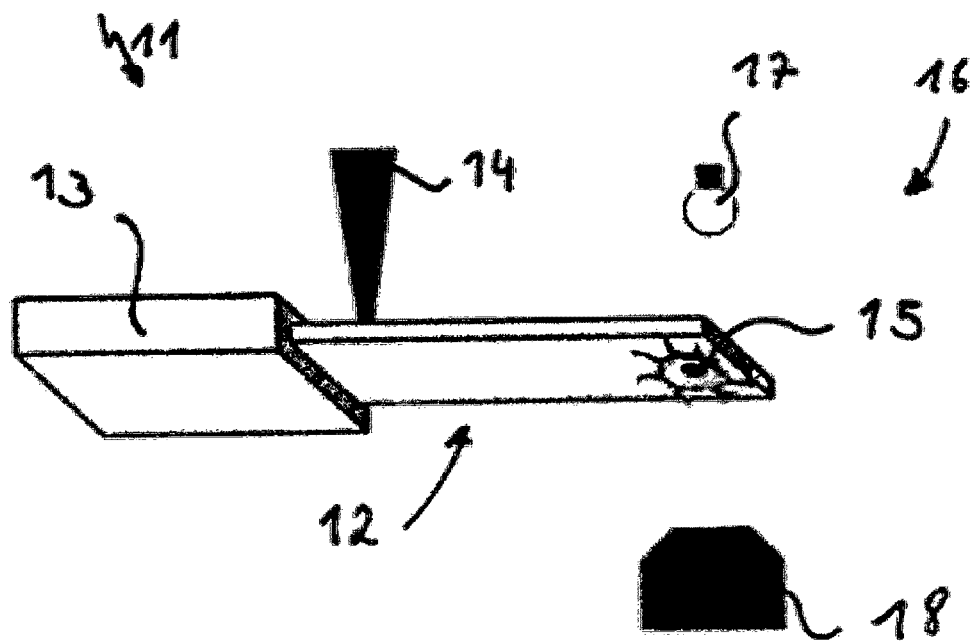
FIG. 2 shows a schematic representation of a measuring device with an optical microscope.

The measuring device 11 according to FIG. 2 comprises a cantilever 12 in a fixation 13 that is excited by an intensity modulated laser at the base of the cantilever 12. Again here, a biological sample 15 is bound by functionalization to the free end of the cantilever 12. Additionally the measuring device 11 is provided through an optical microscope 16 of a light source 17 and a lens system 18. The used microscope 16 is an inverted microscope.

Figure 3:
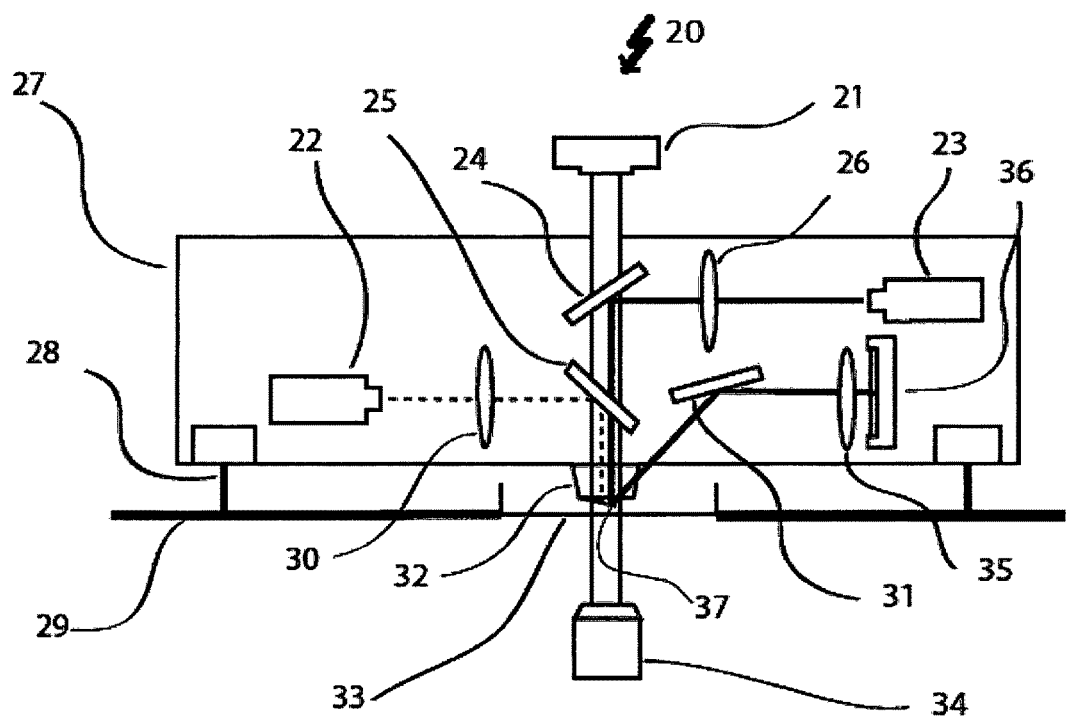
FIG. 3 shows a schematic representation of a measuring device with an optical microscope at a higher level of detail.
Figure 4:
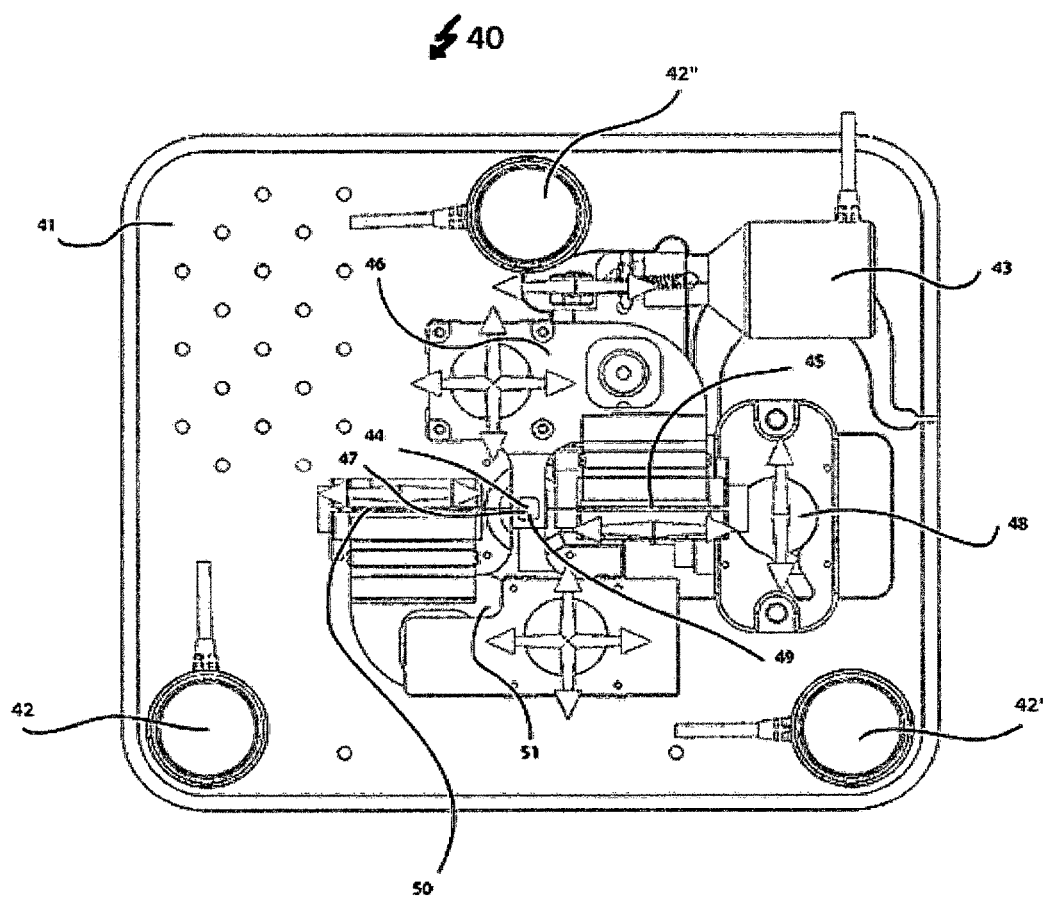
FIG. 4 shows a two-dimensional top view of a measuring device with arrows indicating the directions of movement.
Figure 5:
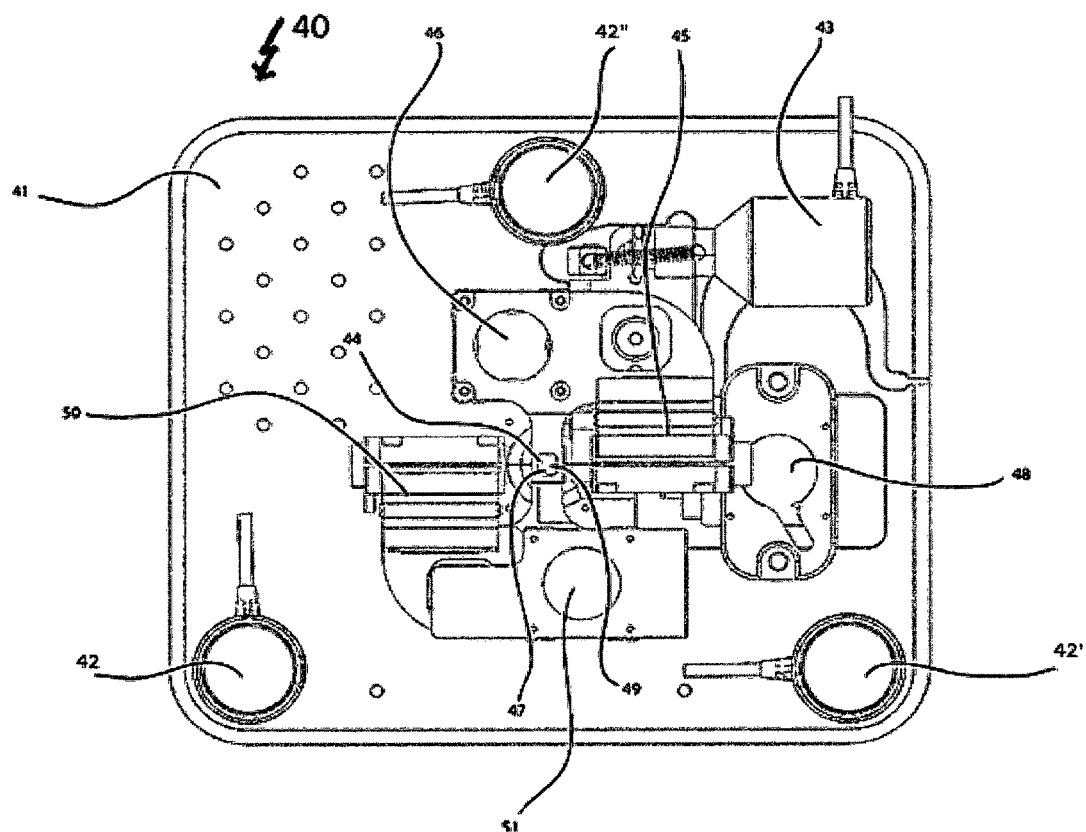
FIG. 5 shows a two-dimensional top view of the measuring device.
Figure 6:
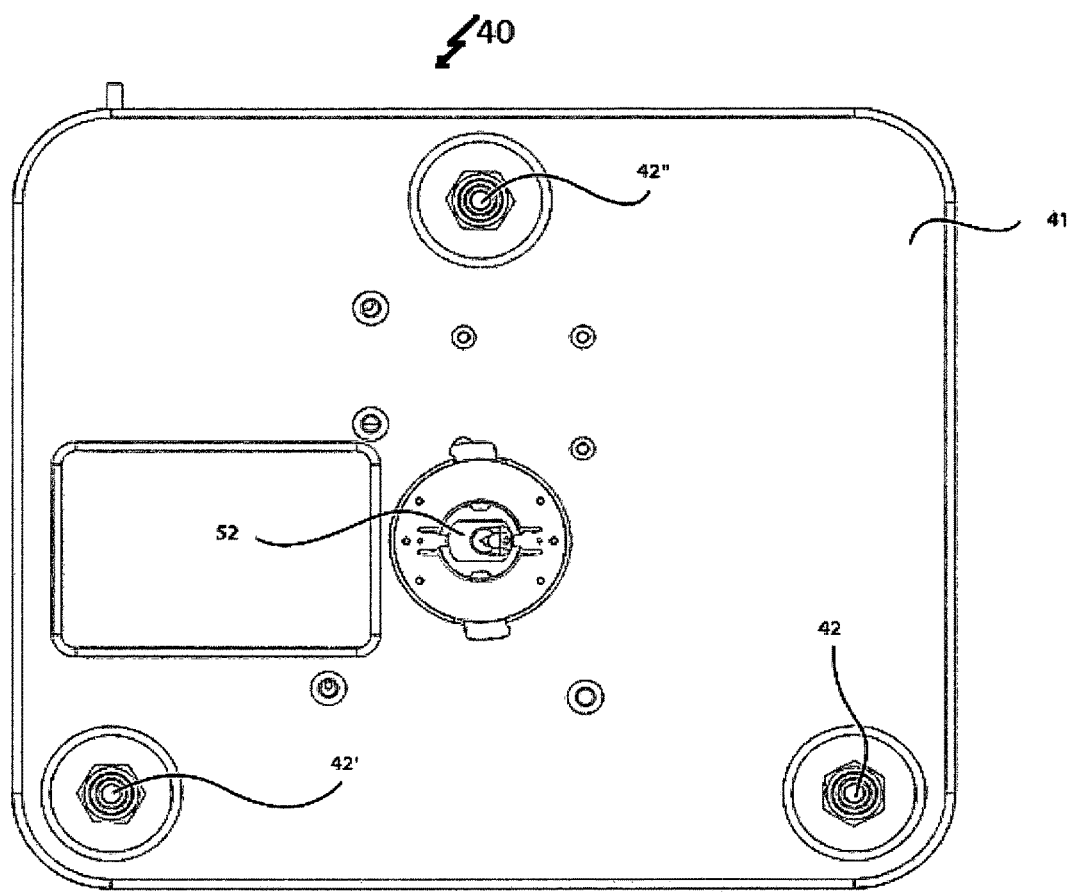
FIG. 6 shows a two-dimensional bottom view of the measuring device.
Figure 7:
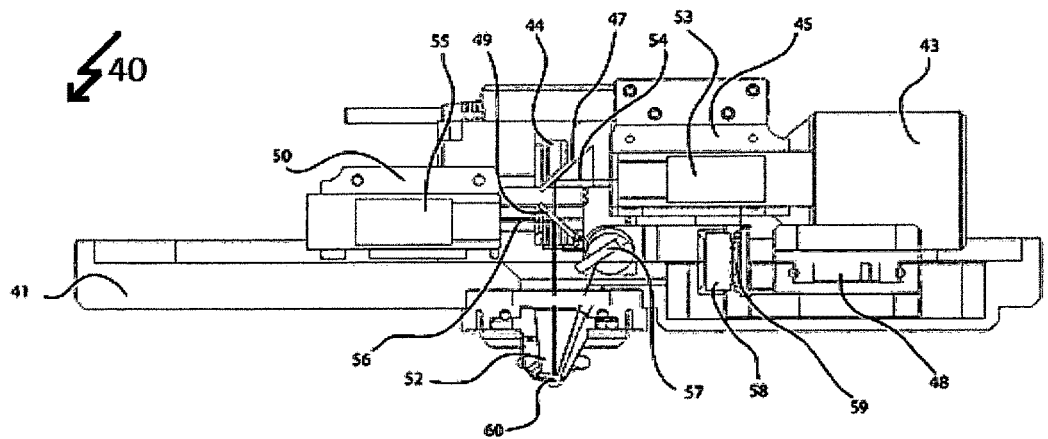
FIG. 7 shows a two-dimensional cross-sectional view of the measuring device.
Figure 8:
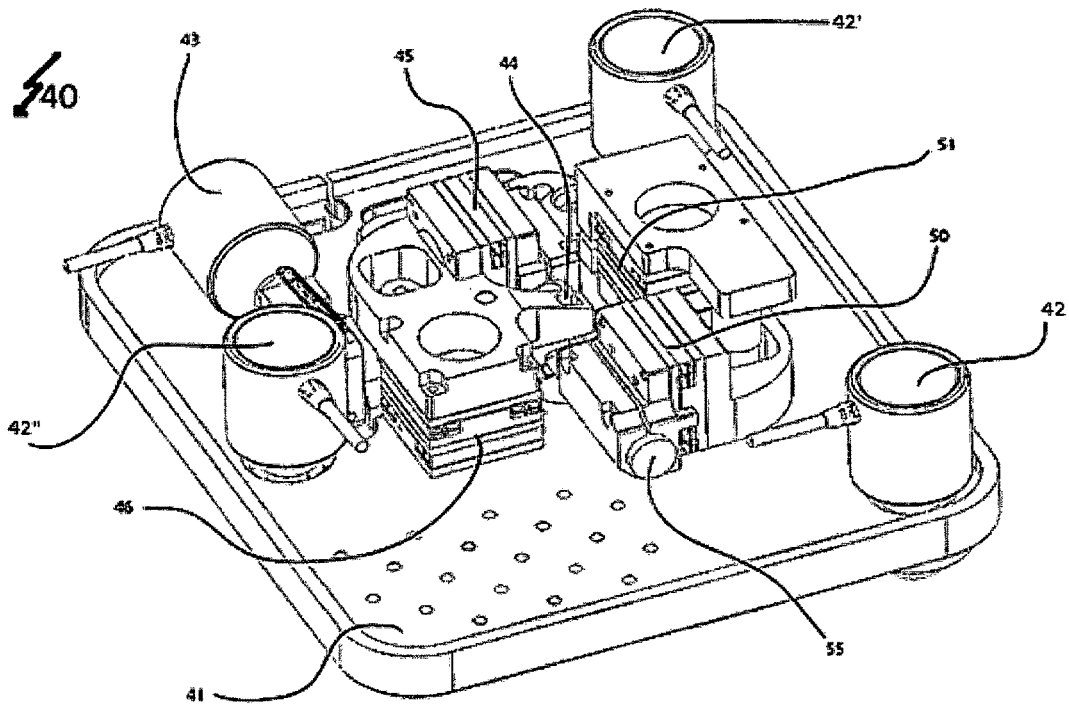
FIG. 8 shows a three-dimensional top view of the measuring device in a first perspective.
Figure 9:
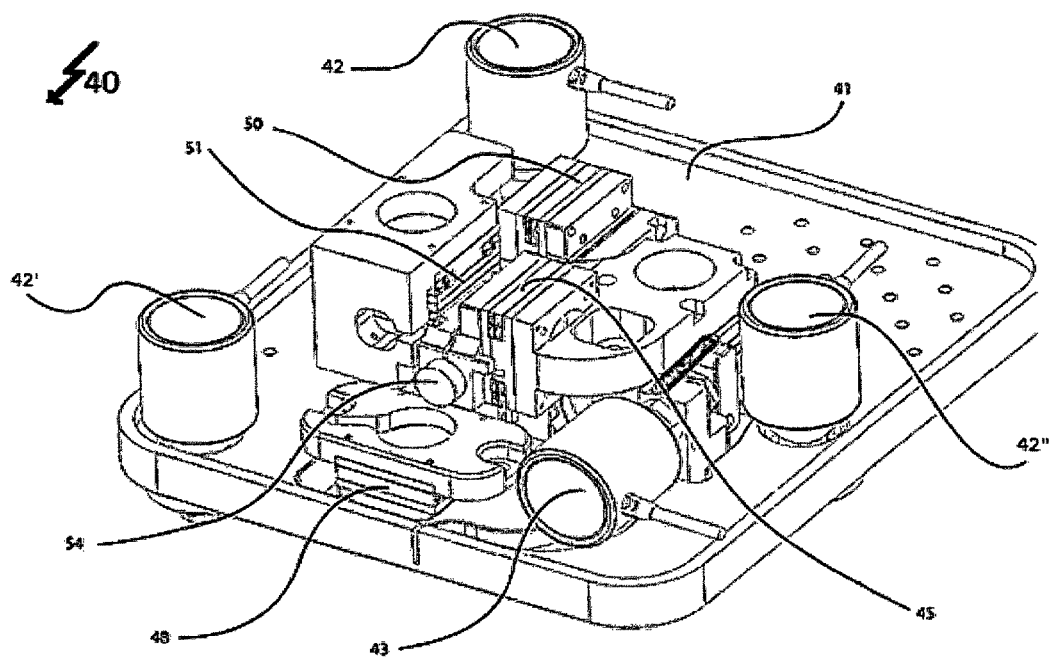
FIG. 9 shows a three-dimensional top view of the measuring device in a second perspective.
Figure 10:
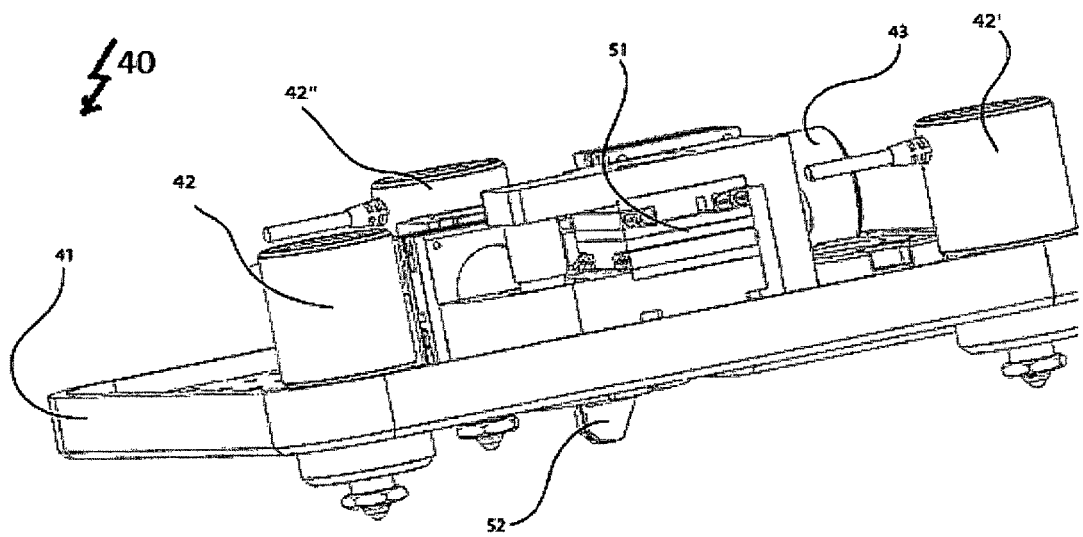
FIG. 10 shows a three-dimensional bottom view of the measuring device.
Figure 11:
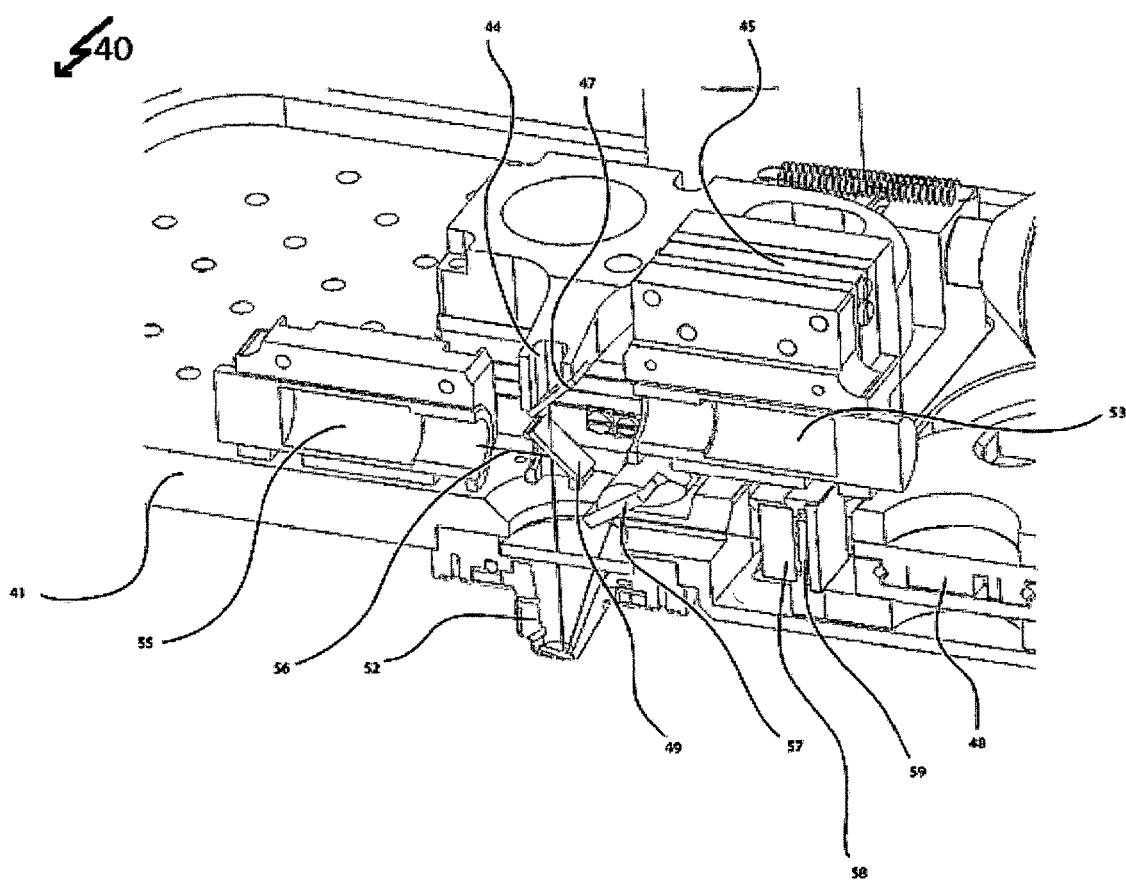
FIG. 11 shows a three-dimensional cross-sectional view in a first perspective.
Figure 12:
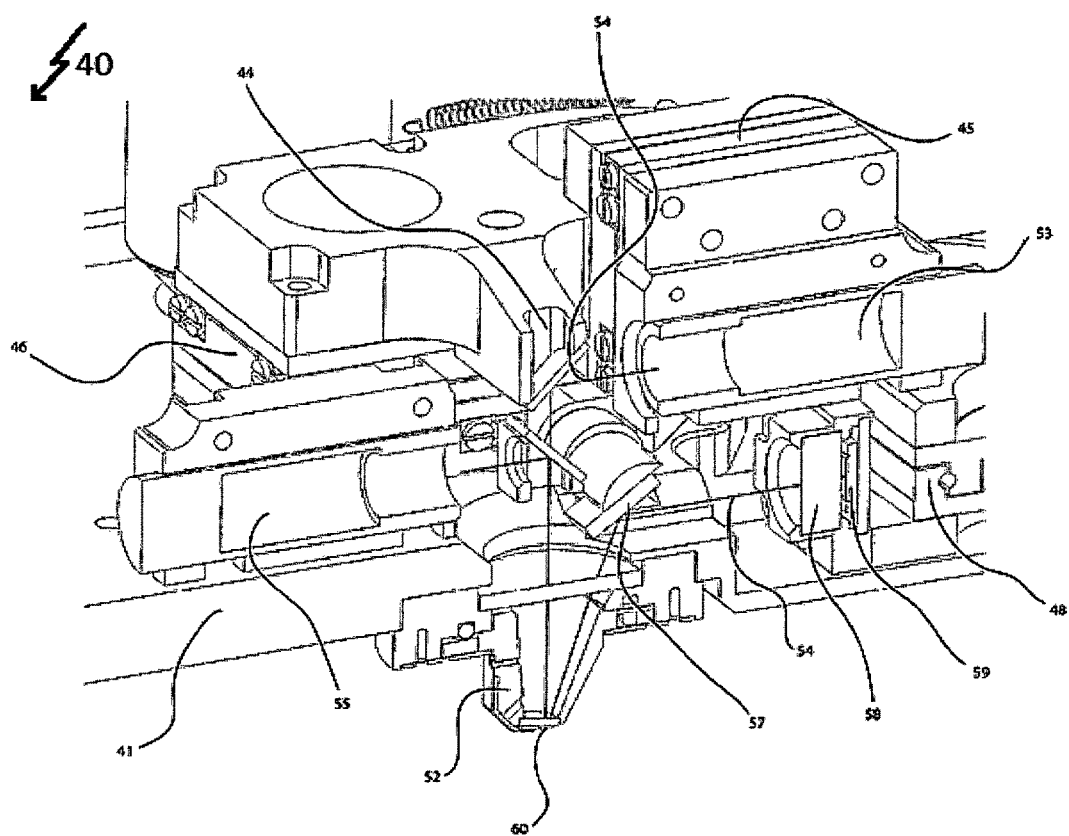
FIG. 12 shows a three-dimensional cross-sectional view in a second perspective.

A measuring device 20 as shown in FIG. 3 combines a measuring device for determining mass mechanical properties of a biological system with an optical technique in cell biology. The DIC or phase contrast illumination 21 together with the inverted microscope 34 forms the respective optical part of the measuring device.

For the part of the measuring device that determines the mass and/or mechanical properties of a biological system the intensity modulated laser 22 emits a laser beam with a wavelength of for example 405 nm that is focused and reflected on the cantilever by the dichroic mirror 25 which reflects the wavelength of the laser, e.g. 405 nm, selectively. The laser spot diameter on the cantilever 37 can be modified by changing the position of the focus of the laser.

The cantilever 37 is held by the cantilever holder 32. A second optical path with the laser 23 reads of the movement of the cantilever 37. This laser 23 operates for example with a wavelength of 850 nm. The laser beam of this second laser (continuous line) is focused on the cantilever by the length system 26 and directed to the cantilever by the dichroic mirror 24 that is reflective for the wavelength of the second laser 23, e.g. 850 nm, selectively. After reflection of the laser beam at the cantilever, the beam is again redirected by the mirror 31 though a bandpass optical filter 35, which is centered at the respective wavelength for example 850 nm before it hits the photodiode 36, which allows detecting the movement the cantilever by detecting the movement of the laser beam. In order to track continuously the mass and/or mechanical properties of the biological sample, the mirror 31 and the photodiode 36 are automatically actuated ensuring that the reflected beam 23 will hit the photodiode at the centre over time. This automatization can be very important since the biological sample can bend the cantilever over time drawing out the laser of the centre of the photodiode. The corrections in the direction of the reflected beam do not disturb the tracking of the resonance frequency of the cantilever. To allow for a movement of the cantilever 37 with respect to the sample, (not shown) i.e. for the device to pick up with the cantilever 37 a certain sample lying on the sample holder 33, e.g. a Petri dish, actuators like actuator 28 are used to move the cantilever in a vertical direction. Additionally, the platform 29 is equipped with two XY-positioners to move the box for the apparatus 27 and the sample holder 33.

A measuring device 40 as shown for a working example in FIGS. 5 to 8 combines a measuring device for determining mass and/or mechanical properties of a biological system with an optical technique in cell biology. However, here, the optical microscope is not shown. Also not shown is a lower part of the measuring device that holds the sample.

The upper part of the measuring device as shown in FIGS. 4 to 12 allows for determining mass and/or mechanical properties of a biological system. A first optical path provides for excitation of the cantilever 60. An intensity modulated laser (not shown) emits a laser beam 56 at a wavelength of 405 nm. This laser beam 56 enters the measuring device 40 through the optical system 55 that focuses the 405 nm laser beam. This optical system 55 is held by two positioner systems a first positioner system 50 and a second positioner system 51. The first positioner system 50 holds the optical system 55 to focus the 405 nm laser beam 56. The first positioner system 50 can move as shown by the arrows in FIG. 4, which for example allows modifying the laser spot diameter on the cantilever 60. A second positioner system 51 holds the first positioner system 50 and the dichroic mirror 49. The dichroic mirror 49 reflects the 405 nm wavelengths allowing other wavelengths in the visual spectrum and the 850 wavelength to go through. This second positioner system 51 can move as shown by the arrows in FIG. 4, which allows positioning the 405 nm laser beam 56 to hit on a certain place as for instance the cantilever 60. This first optical path of the system 40 following the laser beam 56 thereby ensures an adjustable transfer of energy from the intensity modulated laser (not shown) to the cantilever 60. The cantilever 60 itself is held by the cantilever holder 62.

A second optical path following the laser beam 44 with a wavelength of 850 nm reads out the movement of the cantilever 60. This second laser beam 54 enters the measuring device through an optical system 53 to focus the 850 nm laser beam 54. The optical system 53 is held by two positioner systems, a first positioner system 45 and a second positioner system 46. Positioner system 45 holds the optical system 43 to focus the 850 nm laser beam 54. This positioner system 45 can move as shown by the arrows in FIG. 4. This allows for example to modify the laser spot diameter on the cantilever 60. A second positioner system 46 holds the first positioner system 45 and a dichroic mirror 47. The dichroic mirror reflects the 850 nm wavelength, allowing other wavelength in the visual spectrum to go through. Also, this second positioner system 46 can move as shown by the arrows in FIG. 4. This allows for positioning the 850 nm laser beam 54 to hit on a certain place as for instance the cantilever 60. The reflection of the 850 nm laser beam by the cantilever 60 allows this optical path to read out the movement of the cantilever 60 continued by the mirror 57 to address the 850 nm laser beam towards the photodiode 59. The four-quadrant photodiode 59 allows reading out the movement of the cantilever 60 by detecting the position of the 850 μm laser beam 54. The mirror 57 can be rotated to allow positioning of the 850 nm laser beam 54 on the photodiode 59. Therefore, the actuator 43 moves the mirror 57 by spinning the mirror's holder. Additionally, a positioner system 48 allows moving the photodiode 59 as shown by the arrows in FIG. 4. This system for example can be used in combination with the actuator 43 to make the 850 nm laser 54 hit on a certain part of the photodiode 59. Furthermore, this second optical path contains a bandpass filter 58 that is centered at the wavelength of 850 nm. This bandpass filter 58 avoids other wavelengths very different than 850 nm to reach the photodiode 59 thereby increasing the signal to noise ratio for the photodiode 59 to dictate the 850 nm light and avoiding possible disturbances in the detection due to other wavelengths in the system.

The window 44 allows the combination with optical techniques by providing sufficient access for DIC, phase contrast or other illumination types.

The whole system that is placed on the base 41 of the box to hold the apparatus can be moved by the actuators 42, 42' and 42" that allow to move the box and hence the cantilever along the vertical direction. These actuators 42, 42' and 42" for example allow approaching and withdrawing the cantilever 60 to the sample (not shown).

Having described preferred embodiments of the invention, it will be apparent to those skilled in the art to which this invention relates, that modifications and amendments to various features and items can be effected and yet still come within the general concept of the invention. It is to be understood that all such modifications and amendments are intended to be included within the scope of the present invention.

The invention claimed is:

1. A measuring device for determining mass and/or mechanical properties of a biological system comprising a micro-cantilever and an intensity modulated light source exciting the micro-cantilever, wherein the micro-cantilever is functionalized to adhere to the biological system, and wherein the micro-cantilever is at least partially transparent for a wavelength of the visual spectrum.

2. The measuring device according to claim 1, wherein the micro-cantilever is fully immersed in a buffer solution.

3. The measuring device according to claim 1, wherein the micro-cantilever is transparent for a wavelength of the visual spectrum.

4. The measuring device according to claim 1, wherein the measuring device comprises an optical microscope.

5. The measuring device according to claim 4, wherein said optical microscope is at least one selected from the group consisting of a fluorescence microscope, a confocal microscope, a fluorescence energy transfer (FRET) microscope, a DIC and a phase contrast microscope, all of those in particular construed as an inverted microscope.

6. The measuring device according to claim 1, wherein the micro-cantilever has a length in the range of 10 μm to 1000 μm and/or a resonance frequency in a range of 1 Hz to 10 MHz when immersed in water and/or an oscillation amplitude in the range of 0,01 nm to 300 nm and/or the light source is a laser with a wavelength in the range of 350 nm to 750 nm.

7. The measuring device according to claim 6, wherein the micro-cantilever has a length in the range in the size of 10 μm to 100 μm and/or a resonance frequency in the range of 20 kHz to 1200 kHz when immersed in water and/or an oscillation amplitude smaller than 30 nm and/or the light source is a laser with a wavelength in the range of in a range of 350 nm to 550 nm.

8. The measuring device according to claim 7, wherein the micro-cantilever has a resonance frequency in the range of 20 kHz to 400 kHz when immersed in water and/or the light source is a laser with a wavelength in the range of in a range of 350 nm to 450 nm.

9. The measuring device according to claim 1, wherein the light source is focused on a spot and the spot of the light source and the site where the sample is attached are on opposite faces of the cantilever.

10. The measuring device according to claim 1, wherein the light source spot is focused on the base of the cantilever.

11. The measuring device according to claim 1, wherein the light source spot is smaller than 100 μm in diameter.

12. The measuring device according to claim 11, wherein the light source spot is 30 μm in diameter.

13. The measuring device according to claim 11, wherein the light source spot is smaller than 10 μm in diameter.

14. A method for determining mass and/or mechanical properties of a biological system, said method comprising the steps of:
   a. determining a spring constant of a cantilever, in particular a cantilever of a measuring device according to claim 1;
   b. exciting the cantilever with a light source at a certain frequency;
   c. measuring resonance frequency and/or amplitude and phase of the movement of the cantilever before attaching a biological system;
   d. approaching the cantilever to the chosen biological system within the sample;
   e. attaching the biological system to the cantilever;
   f. measuring resonance frequency and/or amplitude and phase of the movement of the cantilever to compare with the resonance frequency obtained in step c); and
   g. computing mass and/or mechanical properties of the biological system.

15. The method according to claim 14, performing the calibration in step a) by:
   a' exciting the cantilever with a laser with a certain frequency; and
   b' measuring the resonance frequency of the cantilever.

16. The method according to claim 14, comprising the additional steps performed before step a) of:
   a" choosing a biological system; and
   b" adapting the cantilever dimensions to the chosen biological system.

17. The method according to claim 16, wherein a feedback loop is used.

18. The method according to claim 17, comprising the step of using the phase of the cantilever as a control variable and the frequency of the signal used to modulate the laser intensity as a manipulated variable.

19. The method according to claim 17, comprising the step of using an oscillation amplitude of the cantilever as the control variable and an amplitude of the signal used to modulate the laser intensity as a manipulated variable.

20. The method according to claim 17, wherein fundamental and/or higher flexural modes of the cantilever are used.

\* \* \* \* \*